United States Patent
De Senna

[11] Patent Number: 5,529,788
[45] Date of Patent: Jun. 25, 1996

[54] ENZYME CONTAINING EFFERVESCENT CLEANING TABLET

[75] Inventor: Richard A. De Senna, Marietta, Ga.

[73] Assignee: Southland, Ltd., Kennesaw, Ga.

[21] Appl. No.: 320,501

[22] Filed: Oct. 7, 1994

[51] Int. Cl.$^6$ ........................................................ A61K 9/46
[52] U.S. Cl. ................... 424/466; 424/94.64; 424/94.65; 424/94.66; 252/174.12
[58] Field of Search .................................. 424/43, 49, 50, 424/466, 93 K–M, 94.64, 94.65, 94.66; 514/2

[56] References Cited

U.S. PATENT DOCUMENTS

| | | | |
|---|---|---|---|
| 4,252,664 | 2/1981 | Inamorato | 252/99 |
| 5,234,832 | 8/1993 | Disch et al. | 435/264 |

*Primary Examiner*—Samuel Barts
*Attorney, Agent, or Firm*—James W. Kayden; Hopkins & Thomas

[57] ABSTRACT

A water-soluble effervescent cleanser tablet comprising at least one proteolytic enzyme, a surfactant and an effervescing agent for use in ultrasonic cleaning equipment.

22 Claims, No Drawings

ENZYME CONTAINING EFFERVESCENT CLEANING TABLET

FIELD OF THE INVENTION

The present invention relates to a method of cleaning dental and medical instruments and equipment and the like. More specifically, the invention relates to a method of preparing a cleaning solution to be used in devices which utilize ultrasonic energy.

BACKGROUND OF THE INVENTION

In the medical and dental fields, instruments and equipment used in examination and treatment are contaminated by various organic materials including blood and tissue fragments. These materials must be removed from the instrument's surface prior to heat sterilization to permit proper sterilization and clean appearance. These solid substances cling to the instruments and equipment and are difficult to remove without the use of mechanical devices, especially after the solids have dried. Hand washing using a brush or other suitable device with detergent followed by rinsing may satisfactorily clean the instruments but is time consuming and is subject to error by the human washer.

It has become common practice to use ultrasonic devices to provide the energy necessary to loosen the soils from dirty instruments and to use various cleaning agents, including detergents, to improve the efficiency of cleaning. A typical cleaning process involves placing the soiled instruments into an ultrasonic cleaning device with warm water and detergent, soaking the instruments for 5 to 120 minutes, applying ultrasonic energy for 15 to 60 minutes, removing the instruments from the device, rinsing with warm water and then sterilizing the instruments. Typically, liquid cleaners containing surfactants, chelating compounds, buffers, and other ingredients are diluted with water in the ultrasonic cleaning device. A typical dilution is one (1) ounce of detergent mixed per one (1) gallon of water. The typical ultrasonic apparatus holds from 1 quart to 5 gallons of solution. Dilutions require the user to pour and measure the required dose of the cleaning solution or the manufacturer of the detergent may provide some type of integrated measuring/dispensing device on its containers. This dose must be mixed with the proper amount of water either in the ultrasonic device if appropriate or in a separate container. As the cleaning solution becomes dirty quickly and should be replaced every one to four cycles and at least every day, large volumes of detergent must be stored and handled. Pouring and measuring, even with devices integrated into the detergent container, is messy and often inaccurate leading to waste and incomplete cleaning.

Due to the proteinaceous nature of the soils common to dental and medical instruments and equipment the use of proteolytic enzymes has been shown effective in improving the removal of these materials from these instruments and equipment. The use of a proteolytic enzyme in combination with a surfactant is taught in U.S. Pat. No. 5,234,832 to Disch et al. which teaches the cleaning and sterilization of medical endoscopes, particularly heat and corrosion sensitive endoscopes made of flexible glass fiber, using a solution of surfactant, proteolytic enzyme and an aldehyde disinfectant. One problem with preparations such as taught by Disch et al, is that storage of liquid enzymes for prolonged periods, especially after dilution and unless refrigerated, can lead to inactivation of the enzyme which reduces or eliminates cleaning performance.

The use of effervescent preparations of cleaning substances has been taught in the prior art. U.S. Pat. No. 4,252,664 to Inamorato, teaches a granular detergent composition with two types of granules, one type containing detergent and the other type containing effervescing agent and other ingredients, which may be a proteolytic enzyme. The composition is taught for use in clothes-washing machines. U.S. Pat. No. 5,055,305 to Young teaches a denture cleansing tablet comprising a bleaching agent and an effervescing agent. U.S. Pat. No. 3,962,107 to Levin et al. teaches a denture cleaning tablet comprising an enzyme and an effervescing agent.

Accordingly, there is a need for an effective cleaning compound for use in cleaning medical and dental instruments and equipment in ultrasonic cleaning devices which eliminates the storage, mixing, handling and waste problems associated with the current products.

SUMMARY OF THE INVENTION

The present invention comprises a water soluble effervescent tablet containing surfactant and enzymes which can be added directly to a cleaning solution such as in an ultrasonic cleaning device. The tablet can also be used to prepare a cleaning solution for use in other cleaning methods such as for cleaning dialysis membranes and evacuation equipment. Thus, it is an object of the present invention to provide a cleaning product to be used for cleaning dental and medical instruments and equipment which is easier to use because it requires no measurement or pre-mixing.

Another object of the present invention is to provide a cleaning product to be used for cleaning dental and medical instruments and equipment which performs better and more reliably than current products.

The surfactants used in the invention are generally non-ionic or anionic types at concentrations sufficient to improve the wetting of the soils and consequently increase the contact between soil and enzyme.

The enzymes used are generally bacterial proteases from the genus Bacillus of the type used in other detergent applications but can also be from other microorganisms, such as from fungus, as for example Aspergillus or Saccharomyces, or may be plant derived proteases such as papain, bromelin, or ticin, or animal derived proteases such as pancreatin, trypsin or pepsin.

The effervescing agent used in the present invention is generally sodium bicarbonate but may be other agents known in the art.

The tablet prepared from the surfactant, enzyme and effervescing agent and other optional ingredients, is of such a size and concentration to allow using whole tablets or multiple tablets directly in ultrasonic devices of different sizes and thus eliminating diluting, mixing and refrigerated storing of diluted liquids. The effervescence provides rapid solubility and mixing of the active ingredients.

DETAILED DESCRIPTION OF THE PREFERRED EMBODIMENT

Most preferably, the cleaning device of the present invention is an ultrasonic device of the type available commercially from a number of manufacturers in various sizes and with various features for controlling time and temperature cycles. For example, Tuttnauer, Ronkonkoma, N.Y. manufactures the "Tutmauer Ultrasonic Cleaner" model U 1424 with a capacity of two (2) quarts and controls for degassing time, sonic time and temperature. The cleaning device may also be a non-ultrasonic device of the type currently used for cleaning dental or medical instruments.

The proteolytic enzymes of the present invention are generally derived from, but not limited to, bacteria of the Bacillus species including *B. subtilis, B. licheniformis* and *B. alkalophilis*. Fungal enzymes derived from *Aspergillus flavus* or *Aspergillus oryzae* are also suitable as are the plant and animal enzymes papain, bromelin, ficin, pancreatin, trypsin and pepsin. These enzymes are available commercially from any of a number of enzyme suppliers at various levels of activity and degrees of purity. Some are also available as aledusted powders or in coated granulated forms for safe handling. The choice of enzyme is dependent upon the composition of the soils to be removed, the type of dental or medical instruments or equipment to be cleaned and the pH and temperature of the final cleaning solution.

The tablet should contain a concentration of proteolytic enzyme sufficient to give from 10,000 to about 1,000,000 Delft units of activity per tablet, and more preferably from about 100,000 to about 300,000 Delft units. The actual concentration of enzyme necessary to give this amount of proteolytic activity will depend upon the specific activity of the enzyme preparation used.

Other enzymes such as lipases or carbohydrases may also be included. Lipases are enzymes which break down lipids, or fats, which are often a component of the soil on the instrument to be cleaned. Thom, et al., U.S. Pat. No. 5,133,893 teaches the combination of a detergent with a lipase. Carbohydrases are enzymes which break down carbohydrates, such as starch, into their component parts.

Cleaning devices for dental and medical instruments are typically operated at a temperature from about 20C. to about 60C. and the cleaning solution preferably is at a pH of about 5 to about 11. The temperature and pH must be compatible with the enzyme or enzymes which are used. If a lipase or carboxylase is used it must also be active at the temperature and pH of the final cleaning solution.

The enzyme must remain active throughout most of the cleaning cycle and preferably throughout several cycles for one full day's use. Therefore the preferred enzymes will be stable in aqueous solutions at pH 5–11 and at temperatures up to 60 C. for several hours.

The surfactants used must be compatible with the enzymes used, should be low foaming and should be compressible low moisture powders suitable for use in effervescent tableting. The surfactant should make up from about 0.1% to about 20% of the tablet weight and more preferably from about 0.5% to 10%. Suitable non-ionic surfactants are polyphenol, ethoxylates, polyglycosides, polysorbate ethers, polyoxyethylene glycol ethers, alkyl polyglycosides, polysorbate ethers, polyoxyethylene ethers, and polyoxypropylene ethers. Suitable anionic surfactants are alcohol sulfates and alcohol ether sulfates.

In addition to the above ingredients, others anticipated include chelating or sequestering agents, enzyme stabilizers and activators, buffers, detergent builders, colors, fragrances, flavors and fillers.

EXAMPLE

Powder concentrate was prepared by blending the following components (all as weight %):

| | |
|---|---|
| 45.6% | Sodium Bicarbonate |
| 23.4% | Deterzyme APUG-380 (a partially granulated protease enzyme formulation manufactured by ENMEX, S.A. de C.V. of Mexico City, Mexico) |
| 24.0% | Citric Acid, anhydrous |
| 5.0% | Sodium Carbonate, anhydrous |
| 0.5% | Sodium Laurel Sulfate |
| 1.0% | Fragrance |
| 0.25% | Magnesium Sterate |
| 0.1% | Color |

Approximately 3 grams of this mixture was compressed in a tableting press to form each tablet.

A test soil was prepared by the following procedure: 250 ml water, 30 g corn starch and 1 package Knox gelatin were mixed and heated to about 100° C. The mixture was cooled to 40°–50° C. and placed with 60 g raw ground beef in a blender. The mixture was blended at high speed for about 2 minutes or until liquified. A capful of red food coloring was added and the mixture blended. Utensils were coated by dipping in the mixture then baking them in a 300° F. oven for ten minutes and then repeating the dipping and baking.

A control cleaning procedure is typically run with 55° C. water in the ultrasonic device. The utensils were soaked for 5 minutes and then ultrasonic energy was applied for 10 minutes. Only about 50% of the coated soil was removed.

This procedure was repeated using a tablet of the present invention dissolved in 2 quart of 25° C. water, then heated to 55° C. All of the soiled coating was removed.

It can thus be appreciated by those skilled in the art that a novel cleaning product and modifications thereof have been shown and described in detail herein. Various additional changes and modifications may be made without departing from the scope of the present invention.

I claim:

1. A method for cleaning dental and medical instruments and equipment which comprises forming a tablet from a mixture of surfactant, at least one proteolytic enzyme and an effervescing agent, dissolving the tablet to form a cleaning solution and contacting the dental and medical instruments and equipment with the cleaning solution.

2. The method of claim 1, wherein the proteolytic enzyme is an enzyme derived from Bacillus.

3. The method of claim 1, wherein the proteolytic enzyme is an enzyme derived from *Bacillus subtilis*.

4. The method of claim 1, wherein the proteolytic enzyme is an enzyme derived from *Bacillus lichenformis*.

5. The method of claim 1, wherein the proteolytic enzyme is an enzyme derived from *Bacillus alkalophilis*.

6. The method of claim 1, wherein the proteolytic enzyme is an enzyme derived from Aspergillus.

7. The method of claim 1, wherein the cleaning solution is contained in an ultrasonic cleaning device which applies sonic energy to the cleaning solution when the dental and medical instruments are in contact with the cleaning solution.

8. The method of claim 1, wherein the proteolytic enzyme comprises from about 1 mg to about 1 g of the tablet.

9. The method of claim 1, wherein the tablet also comprises a lipase.

10. The method of claim 1, wherein the tablet also comprises a carbohydrase.

11. The method of claim 1, wherein the surfactant comprises from about 0.5–10% by weight of the tablet.

12. The method of claim 1, wherein the proteolytic enzyme is derived from a bacteria or a fungus selected from the group consisting of *Bacillus subtilis, Bacillus lichenformis, Bacillus alkalophilis, Aspergillus flavus* and *Aspergillus oryzae*.

13. The method of claim 1, wherein the proteolytic enzyme is selected from the group consisting of papain, bromelin, ficin, pancreatin, trypsin and pepsin.

14. A cleaning product for use in cleaning dental and medical instruments and equipment comprising a tablet formed from a powder mixture of a surfactant, at least one protease and an effervescing agent.

15. The cleaning product of claim 14, wherein the proteolytic enzyme is an enzyme derived from *Bacillus lichenformis*.

16. The cleaning product of claim 14, wherein the effervescing agent comprises a mixture of sodium bicarbonate and citric acid.

17. The cleaning product of claim 14, wherein the tablet also comprises a lipase.

18. The cleaning product of claim 14, wherein the proteolytic enzyme comprises from about 1 milligram to about 1 gram of the tablet weight.

19. The cleaning product of claim 14, wherein the tablet also comprises a carbohydrase.

20. The cleaning product of claim 14, wherein the surfactant comprises from about 0.5 to 10% by weight of the tablet.

21. The cleaning product of claim 14 wherein the protease is derived from a bacteria or a fungus selected from the group consisting of *Bacillus lichenformis, Bacillus subtilis, Bacillus alkalophilis, Aspergillus flavus,* and *Aspergillus orzae*.

22. A cleaning product for use in cleaning dental and medical instruments and equipment, comprising a tablet formed from a mixture of about 0.5 to 10% surfactant, by weight of the tablet, enough protease to provide about 100,000 to 300,000 Delft units, and about 70% effervescing agent, by weight of the tablet.

* * * * *